(12) United States Patent
Tonami

(10) Patent No.: US 8,232,528 B2
(45) Date of Patent: Jul. 31, 2012

(54) NUCLEAR MEDICAL DIAGNOSTIC DEVICE

(75) Inventor: Hiromichi Tonami, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 291 days.

(21) Appl. No.: 12/373,015

(22) PCT Filed: Sep. 19, 2006

(86) PCT No.: PCT/JP2006/318535
§ 371 (c)(1),
(2), (4) Date: Jan. 8, 2009

(87) PCT Pub. No.: WO2008/035399
PCT Pub. Date: Mar. 27, 2008

(65) Prior Publication Data
US 2009/0310735 A1    Dec. 17, 2009

(51) Int. Cl.
*G21K 1/02* (2006.01)
(52) U.S. Cl. .................. 250/363.1; 250/363.04
(58) Field of Classification Search ... 250/361 R–363.1, 250/370.09, 370.11; 378/4, 5, 12
See application file for complete search history.

(56) References Cited

U.S. PATENT DOCUMENTS

| | | | | |
|---|---|---|---|---|
| 6,171,243 B1 * | 1/2001 | Gagnon et al. | ................ | 600/431 |
| 6,175,116 B1 * | 1/2001 | Gagnon et al. | ........... | 250/363.03 |
| 6,342,699 B1 * | 1/2002 | Jeanguillaume | ........... | 250/363.1 |
| 6,448,559 B1 * | 9/2002 | Saoudi et al. | ................. | 250/367 |
| 2003/0189174 A1 * | 10/2003 | Tanaka et al. | ............ | 250/363.03 |

FOREIGN PATENT DOCUMENTS

| JP | H11-72566 | | 3/1999 |
| JP | 2006284346 A | * | 10/2006 |

* cited by examiner

*Primary Examiner* — David Porta
*Assistant Examiner* — Casey Bryant
(74) *Attorney, Agent, or Firm* — J.C. Patents

(57) ABSTRACT

By simultaneously administering a chemical using a nuclear species releasing a single photon (a first chemical) and another chemical using a nuclear species releasing a positron to a subject, the cumulative distributions of the respective chemicals are monitored. A plural number of γ-ray detectors, which are circularly located, and a collimator covering some of the γ-ray detectors and rotates along the front face of the γ-ray detectors are provided. Also, an energy discriminating means for discriminating signals having a single photon γ-ray energy (first signals) from signals having annihilation γ-ray energy (second signals) among all of the signals detected by the detectors is provided. Further, the cumulative position of the first chemical is specified based on the signals corresponding to the γ-ray detectors covered with the rotating collimator from the first signals. On the other hand, the cumulative position of the second chemical is specified by determining the signal almost simultaneously observed form the second signals and the positions thereof on the detectors.

2 Claims, 7 Drawing Sheets

NUCLEAR MEDICAL DIAGNOSTIC DEVICE

BACKGROUND OF THE INVENTION

1. Field of the Invention

The present invention generally relates to a nuclear medical diagnostic device (an emission computed tomography (ECT) device), which applies an radioactive agent to a test subject, and simultaneously measures a γ-ray or a pair of γ-rays emitted by single photon radioactive isotopes (RIs) or positron RIs accumulated in a target portion of the test subject, so as to obtain a tomogram of the target portion.

2. Description of Related Art

For a nuclear medical diagnostic device, that is, an ECT device, the single photon emission computed tomography (SPECT) device and positron emission tomography (PET) device are well known examples thereof.

The SPECT device applies a radioactive agent including the single photon RIs to test subject, and detects the γ-ray emitted from a nuclide by using γ-ray detectors. The energy of the γ-ray emitted from the single photon RIs that are usually used during the inspection of the SPECT device is hundreds of keV. When the SPECT device is used, a single γ-ray is emitted; hence, an incident angle on the γ-ray detector cannot be obtained. Therefore, a collimator is used to detect only the γ-ray incident at a specific angle, so as to obtain the angle information. The detecting method of the SPECT device is as follows. A radioactive agent is applied to a test subject, and the γ-ray generated from the radioactive agent is detected, so as to specify a portion of the test subject where the radioactive agent is consumed relatively more (for example, the portion where cancer cells exist). The radioactive agent contains a material that tends to accumulate on specific tumors or molecules and the single photon RIs, such as Tc-99m, Ga-67, and Tl-201. The obtained data is converted to the data of each voxel through a filtered back projection method and the like. A half life of Tc-99m, Ga-67, and Tl-201 used in the SPECT device is six hours to three days longer than the half life of the RIs used in the PET device.

In another aspect, the PET device applies a radioactive agent including positron RIs to the test subject, and detects an annihilation γ-ray generated by the positrons emitted from the nuclide by using the γ-ray detectors. Theoretically, the positrons may be combined with the electrons of adjacent cells and are annihilated, so the energy of the annihilation γ-ray generated by the positrons emitted from the positron RI used during the inspection of the PET device is fixed to be 511 keV. The annihilation γ-ray generated by the positrons may emit a pair of γ-rays. The detecting method of the PET device is as follows. The radioactive agent and a positron RI O-15, N-13, C-11, or F-18 are applied to the test subject, and the γ-rays generated from the radioactive agent are detected, so as to specify the portion of the test subject where the radioactive agent is consumed relatively more (for example, the portion where cancer cells exist). The radioactive agent includes the material that tends to accumulate on specific cells in the test subject. Fluorodeoxyglucose (2-[F-18]fluoro-2-deoxy-D-glucose, FDG) is an example of the radioactive agent. Through glycometabolism, FDG may be highly accumulated in the tumor tissue, so as to specify the tumor portion. The positrons emitted by the positron emitting nuclide contained in the radioactive agent and accumulated in the specific portion are combined with the electrons of adjacent cells, and are annihilated. A pair of γ-rays having the energy of 511 keV is emitted. The γ-rays are emitted to totally opposite directions from each other (180°±0.6°). If the pair of γ-rays is detected by the γ-ray detectors, it can be recognized that the positrons are emitted between which two γ-ray detectors. By detecting most of the pairs of γ-rays, the portion where the radioactive agent is consumed relatively more may be obtained. For example, as described above, the FDG may be accumulated in the cancer cells with the violent glycometabolism, such that cancer lesions may be found by the PET device. In addition, the obtained data is converted to a radioactive ray generation density of each voxel through the filtered back projection method, so as to pattern the generation position of the γ-ray (the position where the radioactive ray nuclide is accumulated, that is, the position of the cancer cells). O-15, N-13, C-11, and F-18 used in the PET device are RIs with the short half life from 2 min to 110 min.

During the inspection of the PET device, the γ-ray generated when the positrons are annihilated is attenuated in the test subject, so absorption correction data used for the absorption correction must be obtained and the absorption correction data is used to perform the correction. The absorption correction data is as follows. For example, Cs-137 is used as an external ray source, the γ-rays from the external ray source are irradiated on the test subject and the transmission intensity is measured, so as to obtain the data of the attenuation ratio of the γ-ray in the test subject through calculation. The attenuation ratio of the γ-ray in the test subject is estimated by using the obtained absorption correction data, and the data obtained from the emission of the FDG is corrected to obtain a more accurate PET image.

However, the existing nuclear medical diagnostic device has the following problems. That is, in order to improve the diagnostic accuracy, the agent using the nuclide emitting the single photons, an agent using the nuclide emitting the positrons, and other different agents must be simultaneously applied to the test subject. However, the agents cannot be detected and shot simultaneously under the situation. Further, the SPECT device and the PET device are independent from each other, so an expensive device for docking the SPECT device and the PET device docking is required.

SUMMARY OF THE INVENTION

Accordingly, the present invention is directed to a nuclear medical diagnostic device, which is capable of simultaneously detecting and shooting an agent using a nuclide emitting single photons, an agent using a nuclide emitting positrons, and other different agents when the agents are applied to a test subject at the same time.

As embodied and broadly described herein, the present invention has the following characteristic mechanisms.

According to one aspect of the present invention, the nuclear medical diagnostic device includes a plurality of γ-ray detectors, a collimator, a collimator position detecting mechanism, a simultaneous measuring mechanism, an energy discriminating mechanism, a first position specifying mechanism, and a second position specifying mechanism. The plurality of γ-ray detectors is circularly disposed, and converts incident γ-rays to electric signals. The collimator is arranged along the front of the plurality of γ-ray detectors in a rotatable manner, and shields a part of single photons. The collimator position detecting mechanism detects a position of the collimator. The simultaneous measuring mechanism outputs the electric signals that are about simultaneously output from the plurality of γ-ray detectors as simultaneous measuring signals. The energy discriminating mechanism discriminates first signals and second signals among the electric signals output from the plurality of γ-ray detectors, in which the first signals are generated by the single photons emitted from a first agent accumulated in a test subject, and the second signals are generated by positrons emitted from a second agent accumulated in the test subject. The first position specifying mechanism specifies a position of the first agent accumulated in the test subject according to the first signals and the position of the collimator. The second position specifying mechanism specifies a position of the second agent accumulated in the test subject according to the simultaneous measuring signals and the second signals. Thus, the positions of the first agent and the second agent are simultaneously specified by using the above mechanisms.

According to one aspect of the present invention, the collimator is a two-dimensional collimator.

According to one aspect of the present invention, the collimator is a one-dimensional collimator, and includes ceptors arranged in the front of the plurality of γ-ray detectors.

According to one aspect of the present invention, the energy discriminating mechanism further includes a scattered ray removing mechanism, which removes the signals that are about simultaneously measured by the two γ-ray detectors from the first signals, so as to reduce the influence due to the scattered ray of an annihilation γ-ray generated by positrons emitted from the second agent accumulated in the test subject.

EFFECT OF THE INVENTION

In the nuclear medical diagnostic device according to the present invention, even if the agent using the nuclide emitting single photons, agent using the nuclide emitting positrons, and other different agents are simultaneously applied to the detected body to improve a diagnostic accuracy, the agents can still be detected and shot simultaneously.

The detectors having the SPECT function and the PET function are shared, so as to provide the detectors with a reasonable price.

Only the collimator is rotated, and the γ-ray detectors are not required to move; hence, noise signals resulting from vibration are prevented.

If the ceptors are disposed in the front of the detectors, the collimator is designed to be one dimensional. Therefore, the rotating collimator is light in weight, such that the collimator may be rotated by using a smaller driving mechanism.

When the positron annihilation γ-ray is incident on the γ-ray detector as the γ-ray with the same energy as the single photons through Compton scattering, the positron annihilation γ-ray is discriminated as the electric signal caused by the single photons by the energy discriminating mechanism. However, a pair of annihilation γ-rays is emitted after the Compton scattering. Accordingly, by removing the simultaneously measured signals, a high quality image, in which the effect of the scattered ray is reduced, may be obtained.

Further, by determining the types of the nuclides contained in the agents, portions of cancer cells where the FDG radioactive agent is accumulated are specified, and the diseased portions, except for the portions where the radioactive agent including the single photon RI is accumulated, are also specified.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
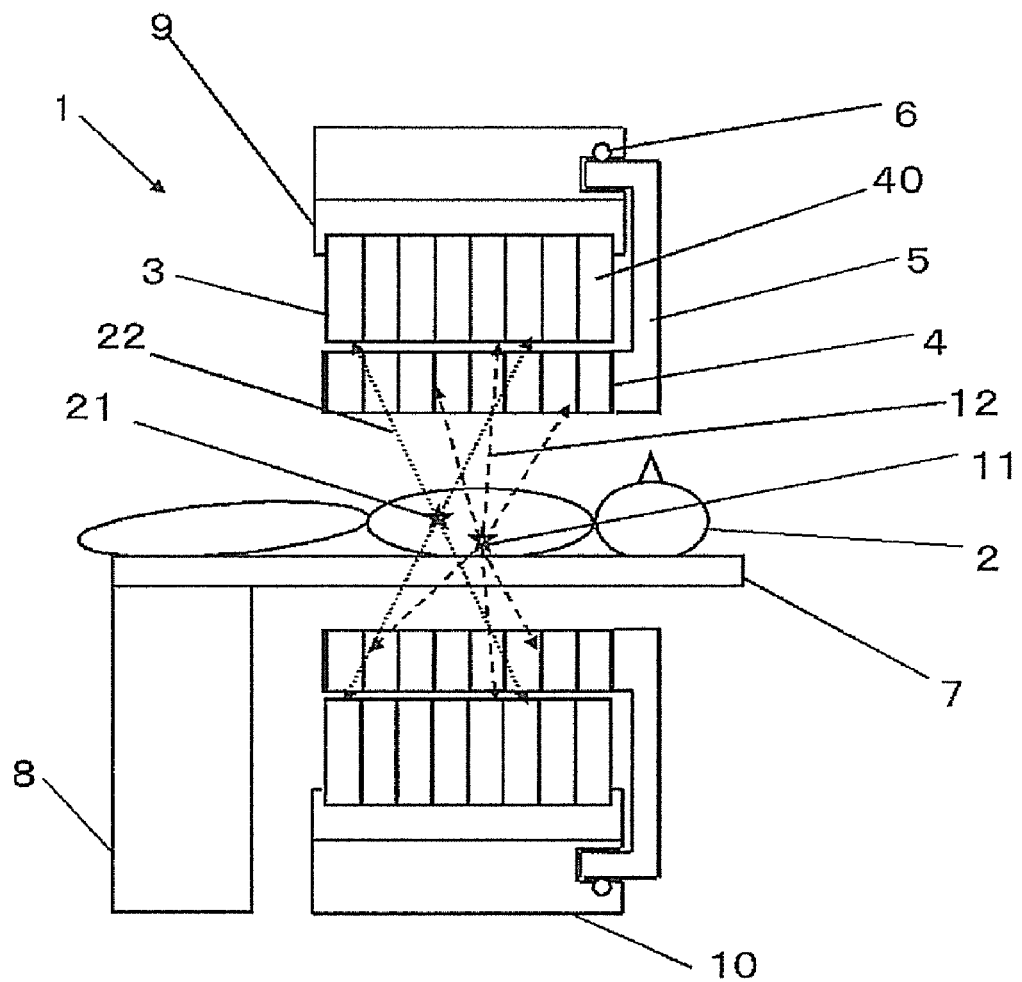
FIG. 1 is a cross-sectional view of a nuclear medical diagnostic device according to a first embodiment of the present invention.

Reference will now be made in detail to the present embodiments of the invention, examples of which are illustrated in the accompanying drawings. Wherever possible, the same reference numbers are used in the drawings and the description to refer to the same or like parts.

First Embodiment

The structure of a nuclear medical diagnostic device according to the first embodiment of the present invention is shown in the drawings and is described in the following. FIG. 1 is a cross-sectional view of a nuclear medical diagnostic device 1 of the present invention. It is assumed that in order to improve a diagnostic accuracy, an agent using a nuclide emitting single photons, an agent using a nuclide emitting positrons, and other different agents are simultaneously applied to a test subject 2 lying on a bed 7.

FIG. 1 shows that an accumulation portion 11 of an agent with single photons emitting nuclide is present and shows an accumulation portion 21 of an agent with positrons emitting nuclide is present in the test subject 2.

In this embodiment, it is assumed that the first agent includes the nuclide formed by Tc-99m emitting the single photons. The energy of the γ-ray of the nuclide is 141 keV, and the half life is 6 hours.

In another aspect, it is assumed that the second agent includes the nuclide formed by FDG emitting the positrons. The nuclide emits the positrons, which are combined with the electrons of adjacent cells and are annihilated, and emits a pair of γ-rays having the energy of 511 keV. Further, the half life is 110 min.

The nuclear medical diagnostic device of the present invention simultaneously shoots, patterns, and specifies the positions of the agents accumulated in the test subject. In this embodiment, a γ-ray detector 3 is used to detect both the agent using the nuclide emitting the single photons and the agent using the nuclide emitting the positrons.

As described above, in order to detect a single photon γ-ray 12, a two-dimensional collimator 4 is required. Under the situation of the embodiment of FIG. 1, the two-dimensional collimator 4 is combined by a circular supporting means 5 residing on the entire periphery. The supporting means 5 is guided by a bearing 6 arranged on a seat frame 10, and may be rotated by using an external driving mechanism (not shown). Here, the two-dimensional collimator 4 is formed by a shielding material two-dimensionally combined in a lattice shape.

The γ-ray detector 3 is formed by a γ-ray detector module 40. The γ-ray detector 3 is circularly disposed opposite to a regulated tomogram surface and is stacked for several layers along a body axis direction of the test subject 2.

Figure 2:
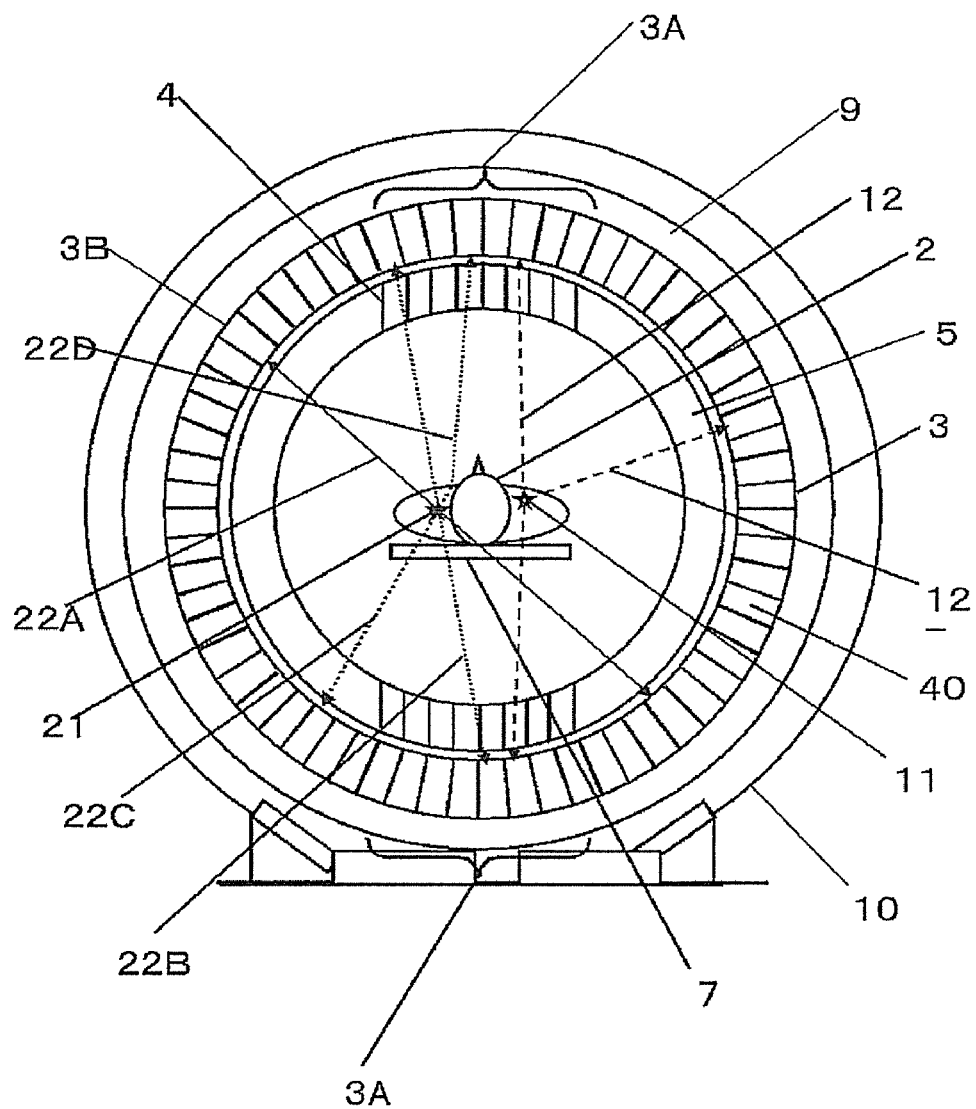
FIG. 2 is a front sectional view of the nuclear medical diagnostic device according to the first embodiment of the present invention.

In another aspect, FIG. 2 is a front sectional view of the nuclear medical diagnostic device 1 of the present invention. The two-dimensional collimator 4 is arranged along the front of the γ-ray detector 3 in a rotatable manner, and the γ-ray detector 3 is circularly disposed opposite to the regulated tomogram surface. Further, the two-dimensional collimator 4 only resides on a part of the entire periphery, and is arranged at opposite positions. In this embodiment, the two-dimensional collimator is arranged at opposite positions, but the two-dimensional collimator is unnecessarily arranged at opposite positions.

The two-dimensional collimator 4 is an indispensable part for detecting the single photon γ-ray 12. That is, when the two-dimensional collimator 4 rotates, at the moment the two-dimensional collimator 4 overlaps with the γ-ray detectors 3 which are circularly disposed relative to the regulated tomogram surface, the γ-ray detector 3A located in the overlap region functions together with the two-dimensional collimator 4, so as to detect the single photon γ-ray 12. All the γ-ray detectors 3 detect annihilation γ-rays 22 generated from the positrons. In addition, lead, tungsten, tungsten alloy, molybdenum, tantalum, and other heavy metals are used as the shielding material of the two-dimensional collimator 4.

In this aspect of the invention, the γ-ray detector module 40 forming the γ-ray detector 3 is composed of scintillators, a light guide, and photomultipliers, in which the scintillators will emit light after the γ-rays emitted from the radioactive agent in the test subject are incident thereon. The light guide is used to specify the position, and the photomultipliers convert the light emitted by the scintillators to a pulse electric signal. In order to have a detailed description of the γ-ray detector module 40, an example is shown in FIGS. 3 and 4.

Figure 3:
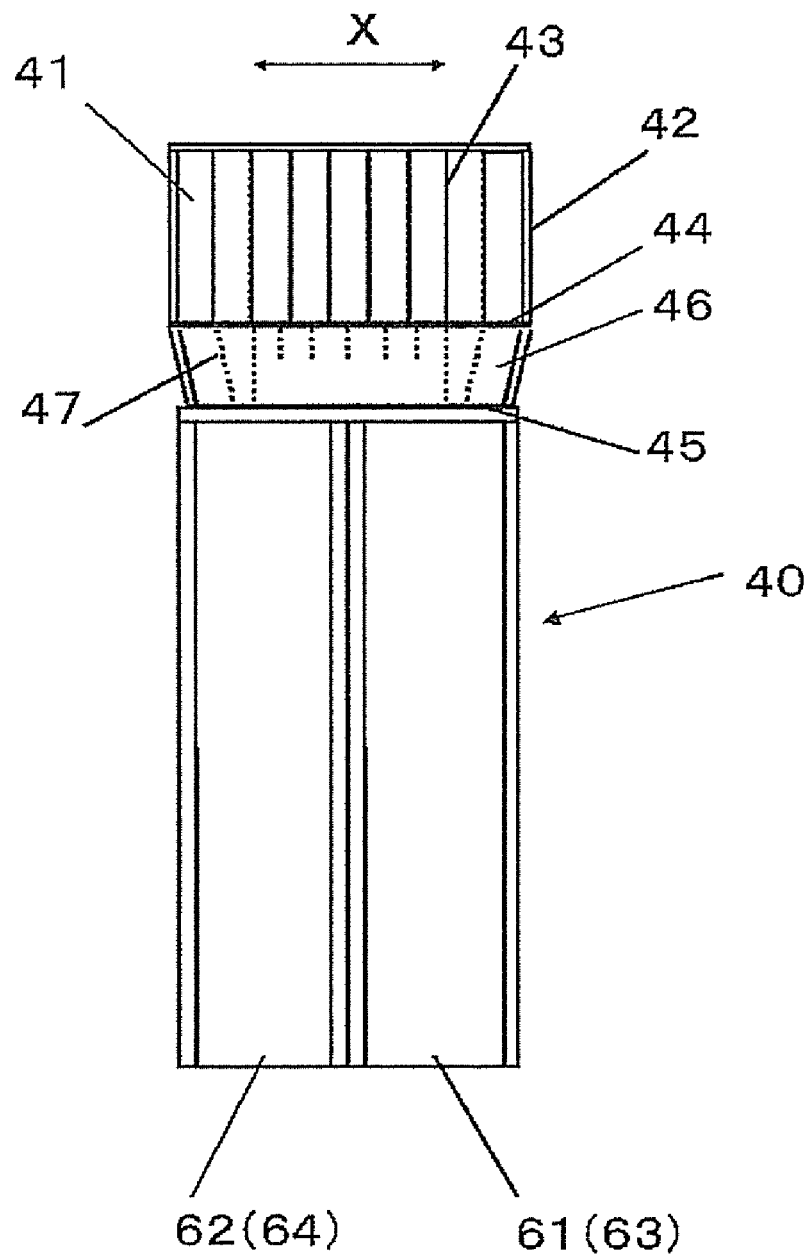
FIG. 3 is an outside view of a γ-ray detector of the present invention observed from an X direction.
Figure 4:
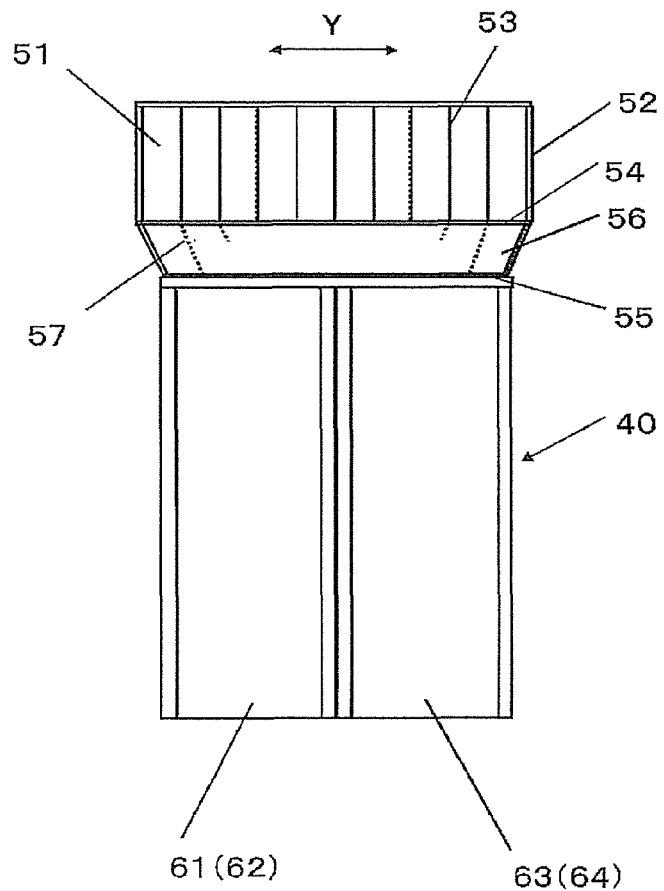
FIG. 4 is an outside view of the γ-ray detector of the present invention observed from a Y direction.

FIG. 3 is an outside view in an X direction (side view) of the γ-ray detector module 40 observed from a Y direction, and FIG. 4 is an outside view in the Y direction (front view) of the γ-ray detector module 40 observed from the X direction. The γ-ray detector 3 is constructed with a scintillator array 42 (52), a light guide 46 (56), and four photomultipliers 61, 62, 63, and 64. The scintillator array 42 (52) has scintillators 41 (51) that are two-dimensionally and compactly arranged. The scintillators 41 (51) are divided by appropriately sandwiching light reflective materials 43 and 53, and 90 scintillators 41(51) are arranged in a manner of nine scintillators in the X direction and ten scintillators in the Y direction. The light guide 46 (56) is optically combined with the scintillator array 42 (52) and includes embedded lattice frames combined with light reflective materials 47 and 57, and is divided into a plurality of small areas. The four photomultipliers 61, 62, 63, and 64 are optically combined with the light guide 46 (56), respectively. In addition, the photomultipliers 61 and 62 are shown in FIG. 3, and the photomultipliers 63 and 64 are shown in FIG. 4. In this aspect of the invention, the scintillators 41 (51) apply, for example, inorganic crystals such as $Gd_2SiO_5$:Ce, $Gd_2SiO_5$:Ce doped with Zr, $Lu_2SiO_5$:Ce, LuYSiO$_5$:Ce, $LaBr_3$:Ce, $LaCl_3$:Ce, LuI:Ce, $Bi_4Ge_3O_{12}$, or $Lu_{0.4}Gd_{1.6}SiO_5$:Ce etc.

As shown in FIG. 3, when the γ-ray is incident on the nine scintillators 41 arranged in the X direction (in the X direction, the light reflective material 43 is sandwiched between every two scintillators 41), the γ-ray is converted to a visible light. The light is guided to the photomultipliers 61-64 through the optically combined light guide 46. Here, the position, length, and angle of each light reflective material 47 in the light guide 46 are adjusted, such that an output ratio of the photomultiplier 61 (63) and the photomultiplier 62 (64) arranged in the X direction is changed according to a fixed proportion.

In more detail, if the output of the photomultiplier 61 is set to P1, the output of the photomultiplier 62 is set to P2, the output of the photomultiplier 63 is set to P3, and the output of the photomultiplier 64 is set to P4, the position and the length of the light reflective material 47 are set, such that a calculated value $\{(P1+P3)-(P2+P4)\}/(P1+P2+P3+P4)$ representing a position in the X direction is changed according to the position of each scintillator 41 according to the fixed proportion.

In another aspect, as shown in FIG. 4, for the ten scintillators 51 arranged in the Y direction (the light reflective material 53 is not sandwiched between the four scintillators 51 in the center, but is sandwiched between every two scintillators 51 except for the four scintillators 51 in the center), the situation is the same, the light is guided to the photomultipliers 61-64 through the optically combined light guide 56. In other words, the position and the length of each light reflective material 57 in the light guide 56 are set, and the angle is adjusted under an inclined situation, such that the output ratio of the photomultiplier 61 (62) and the photomultiplier 63 (64) arranged in the Y direction is changed according to the fixed proportion.

In essence, the position and the length of the light reflective material 57 are set, such that a calculated value $\{(P1+P2)-(P3+P4)\}/(P1+P2+P3+P4)$ representing a position in the Y direction is changed according to the position of each scintillator 51 based on the fixed proportion.

In this aspect of the invention, the light reflective material 43 (53) between the scintillators 41 (51) and the light reflective material 47 (57) of the light guide 46 (56) may use a multi-layer film of silicon oxide and titanium oxide using a polyester film as a base material. A reflection efficiency of the multi-layer film is quite high, so it is used as a light reflective element. However, strictly speaking, a transmission component is generated according to the incident angle of the light, so the transmission component must also be calculated to decide the shapes and the arrangement of the light reflective material 43 (53) and the light reflective material 47(57).

In addition, the scintillator array 42 (52) is bound with the light guide 46 (56) by using a coupling binding agent 44 (54), and the light guide 46 (56) is bound with the photomultipliers 61-64 by using a coupling binding agent 45 (55). Except for an optically combined surface with the photomultipliers 61-64, the peripheral surfaces not opposite to each scintillator 41 (51) are covered by the light reflective material. In this aspect of the invention, the light reflective material mainly uses a fluorine resin tape.

Figure 5:
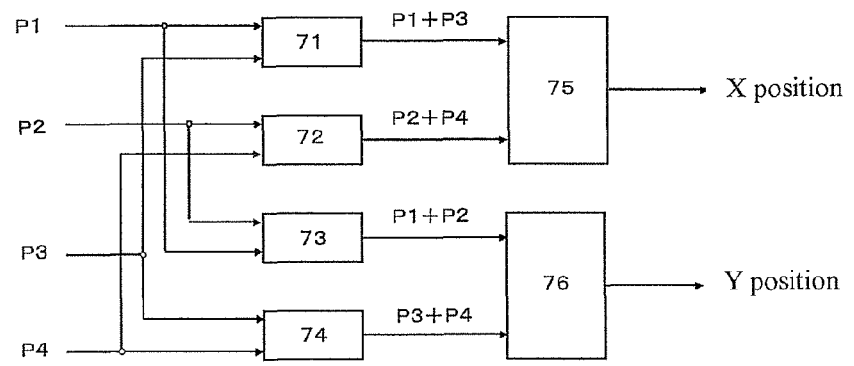
FIG. 5 is a schematic view of an example of a position operating circuit of the γ-ray detector of the present invention.
Figure 6:
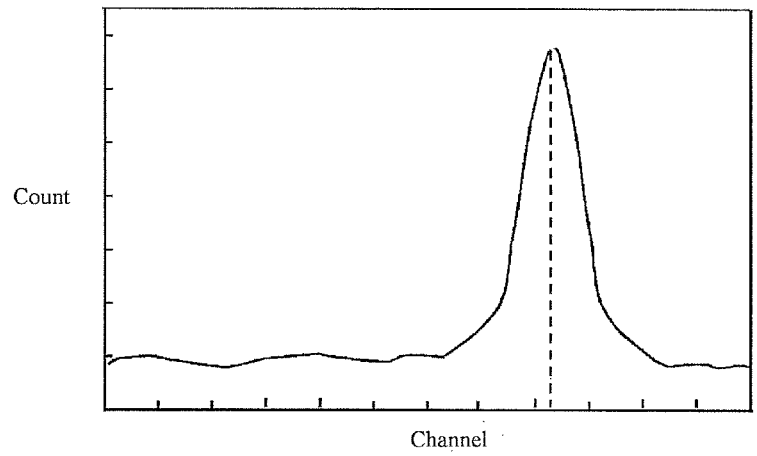
FIG. 6 is an energy spectrum of the γ-ray detector of the present invention.

FIG. 5 is a block diagram of a structure of a position operating circuit of the γ-ray detector. The position operating circuit is formed by adders 71, 72, 73, and 74, and position recognizing circuits 75 and 76. As shown in FIG. 5, in order to detect the incident position of the γ-ray in the X direction, the output P1 of the photomultiplier 61 and the output P3 of the photomultiplier 63 are input to the adder 71, and the output P2 of the photomultiplier 62 and the output P4 of the photomultiplier 64 are input to the adder 72. Each added output (P1+P3) and (P2+P4) of the two adders 71 and 72 is input to the position recognizing circuit 75. According to the two added outputs, the incident position of the γ-ray in the X direction is obtained. Similarly, in order to detect the incident position of the γ-ray in the Y direction, the output P1 of the photomultiplier 61 and the output P2 of the photomultiplier 62 are input to the adder 73, and the output P3 of the photomultiplier 63 and the output P4 of the photomultiplier 64 are input to the adder 74. Each added output (P1+P3) and (P2+P4) of the two adders 73 and 74 is input to the position recognizing circuit 76. According to the two added outputs, the incident position of the γ-ray in the Y direction is obtained. Further, the calculated value (P1+P2+P3+P4) represents the energy relative to the event, and is shown as the energy spectrum in FIG. 6.

Figure 7:
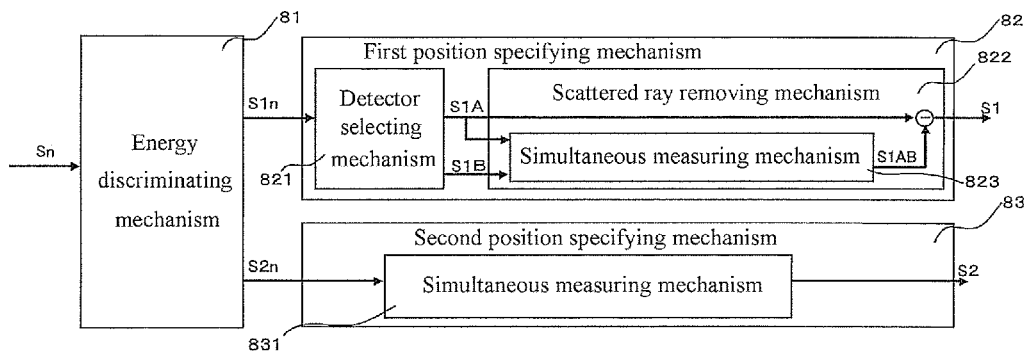
FIG. 7 is a block diagram of a discriminating function of the present invention.
Figure 8:
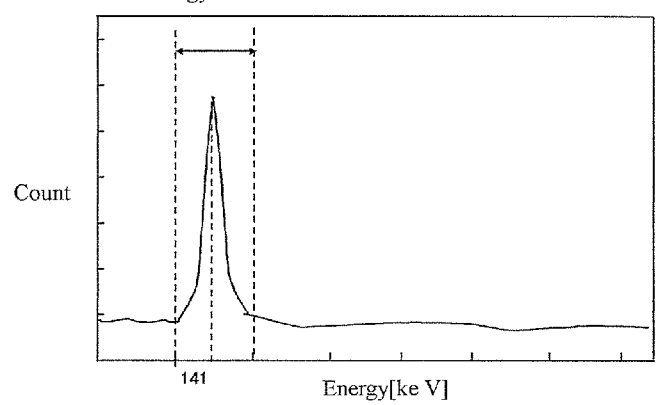
FIG. 8 is a schematic view of the energy spectrum and an energy window of the γ-ray detector of the present invention.
Figure 9:
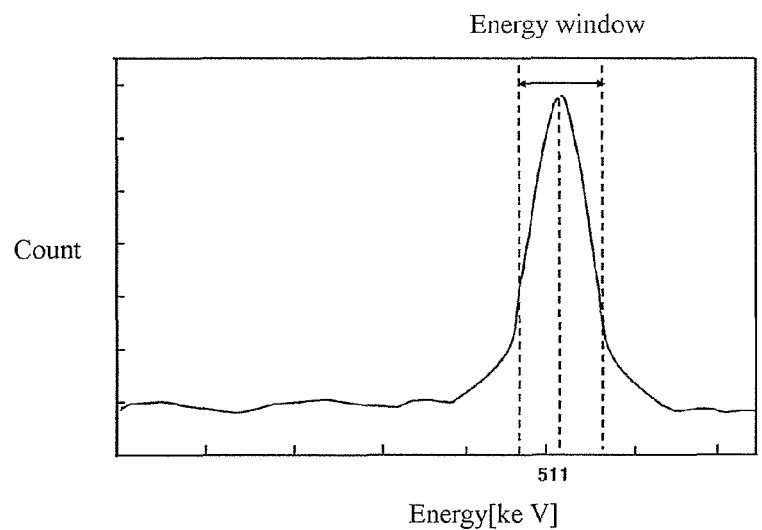
FIG. 9 is a schematic view of the energy spectrum and an energy window of the γ-ray detector of the present invention.

Then, referring to FIGS. 7-9, the structure for detecting the annihilation γ-ray generated by the positrons and the single photon γ-ray is described in detail.

FIG. 7 is a schematic block diagram of the process for detecting the annihilation γ-ray generated by the positrons and the single photon γ-ray. In this aspect of the invention, it is assumed that N γ-ray detectors 3 are installed in the device. The electric signals Sn (n=1, 2, ... N) output from all the γ-ray detectors 3 are output to an energy discriminating mechanism 81. As shown in FIG. 8, in the energy discriminating mechanism 81, an energy window centered at 141 keV (for example, ±100 keV) is set on the energy spectrum, and the signals entering the energy window are output as first signals S1n. As shown in FIG. 9, an energy window centered at 511 keV (for example, ±100 keV) is set on the energy spectrum, and the signals entering the energy window are output as second signal S2n.

The first signals S1n output from the energy discriminating mechanism 81 are input to a first position specifying mechanism 82. The first position specifying mechanism 82 outputs a signal S1 used to specify the position of the first agent. As shown in FIGS. 1 and 2, in order to specify the position of the first agent, the single photon γ-ray 12A passing through the rotating two-dimensional collimator 4 and reaching the γ-ray detector 3A must be used as the single photon γ-ray for detection.

In one aspect of the invention, the position of the two-dimensional collimator 4 is detected in sequence by using a collimator position detecting mechanism (not shown). Therefore, a detector selecting mechanism 821 is disposed. The detector selecting mechanism 821 divides the first signals S1n output from the energy discriminating mechanism into signals S1A from the γ-ray detector 3A overlapping the two-dimensional collimator 4 and signals S1B from the γ-ray detector 3B not overlapping the two-dimensional collimator 4, and outputs the signals S1A and S1B. When the collimator 4 is rotated, the signals S1A are counted, so as to correctly specify the accumulation portion 11 of the first agent.

However, as shown in FIG. 2, a Compton scattered ray 22D presents in the annihilation γ-ray 22 starting from the accumulation portion 21 of the second agent. The Compton scattered ray 22D also causes Compton scattering in the test subject 2 as the annihilation γ-ray 22C does, changes the traveling path, and reduces the energy, and is then emitted. The Compton scattered ray 22D has, for example, the energy of approximately 141 keV, and reaches the γ-ray detector 3A after passing through the rotating two-dimensional collimator 4. At this time, the accumulation portion 21 of the second agent may be mistaken as the accumulation portion of the first agent. In order to solve the problem, it is preferably for a scattered ray removing mechanism 822 to be disposed in the first position specifying mechanism 82.

In the scattered ray removing mechanism 822, the signals S1A and S1B are input, signals S1AB entering the time window (for example, within 6 ns) are detected by a simultaneous measuring mechanism 823, and the signals S1AB are removed from the signals S1A. Through the process, the effect of the annihilation γ-ray with its energy reduced after the Compton scattering may be eliminated.

In another aspect, the second signals S2n output from the energy discriminating mechanism 81 are input to a second position specifying mechanism 83. The second position specifying mechanism 83 has a function of specifying the position of the second agent.

The second position specifying mechanism 83 extracts the signals S2 measured simultaneously by a simultaneous measuring mechanism 831 at two positions. The simultaneous measuring mechanism 831 extracts the signals entering the time window (for example, within 6 ns) as the annihilation γ-ray signals S2. According to the two positions of the signals where the signals are observed, the position of the second agent is specified.

In this manner, the energy discriminating mechanism 81 extracts the signals S1n and S2n with the required energy from the signals S1n output from all the γ-ray detectors, and the simultaneous measuring mechanism 831 of the annihilation γ-ray detecting mechanism 83 extracts the signals related the annihilation γ-rays approximately 180° opposite to each other and emitted in pairs.

In one aspect of the invention, it may also be considered that a part of the annihilation γ-rays 22 that should be incident on the γ-ray detector 3A originally is shielded by the two-dimensional collimator 4. However, the energy of the annihilation γ-ray 22 is greater than 511 keV, so the annihilation γ-rays 22 may pass through the two-dimensional collimator 4. According to the material of the collimator 4, a fixed amount of annihilation γ-rays 22B are shielded according to a certain probability.

As described above, the nuclear medical diagnostic device of the present invention may simultaneously shoot, pattern, and specify the positions of the agents accumulated in the test subject. In the present invention, the γ-ray detector 3 is used to detect both the agent using the nuclide emitting the single photons and the agent using the nuclide emitting the positrons.

Second Embodiment

The nuclear medical diagnostic device according to the second embodiment of the present invention is described in the following.

Figure 10:
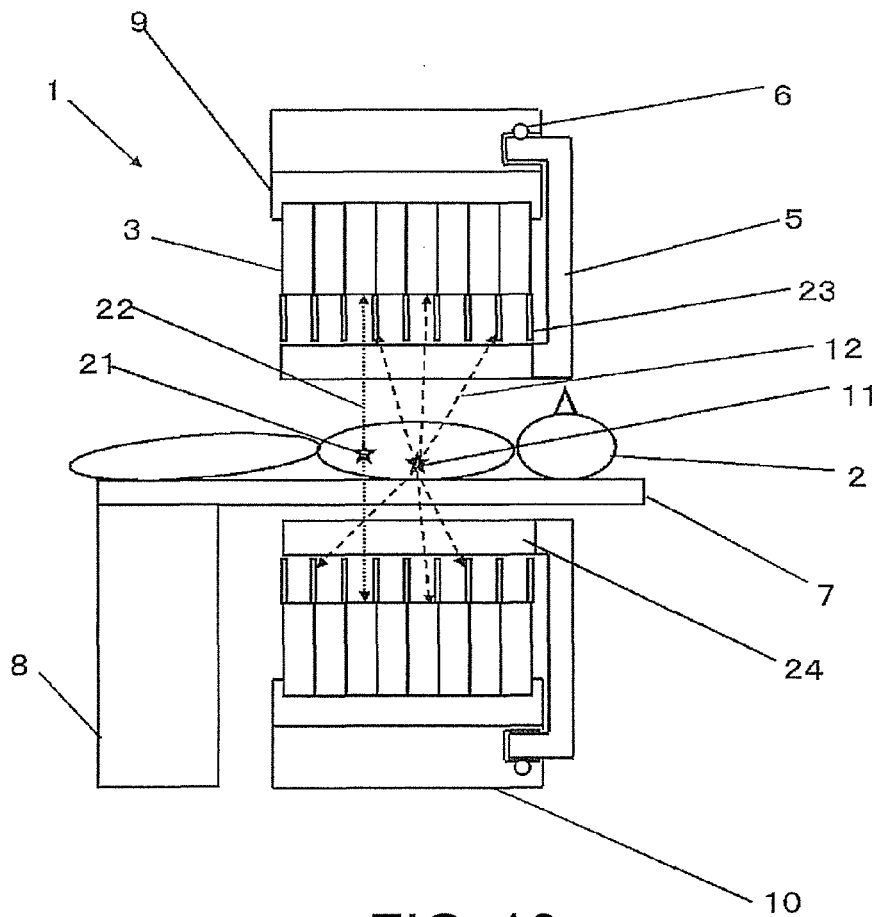
FIG. 10 is a cross-sectional view of a nuclear medical diagnostic device according to a second embodiment of the present invention.

FIG. 10 is a cross-sectional view of the nuclear medical diagnostic device according to the second embodiment of the present invention. Similar to the first embodiment, it is assumed that an agent using a nuclide emitting single photons, an agent using a nuclide emitting positrons, and other different agents are simultaneously applied to a test subject 2 lying on a bed 7 to improve the diagnostic accuracy.

FIG. 10 shows that an accumulation portion 11 having the agent using the nuclide emitting the single photons and an accumulation portion 21 having the agent using the nuclide emitting the positrons exist in the test subject 2.

As described above, in order to detect the single photon γ-ray 12, a two-dimensional collimator is required. Under the situation of the second embodiment of FIG. 10, ceptors 23 are arranged on the whole periphery in the front of the γ-ray detector 3, so as to perform the two dimensional collection during the detection of the positrons. In another aspect, a one-dimensional collimator 24 is combined by a circular supporting means 5 configured on the whole periphery. The supporting means 5 is guided by a bearing 6 arranged on a seat frame 10, and may be rotated by an external driving mechanism (not shown). The one-dimensional collimator 4 has a shielding material arranged in a direction. In other words, the part on which the ceptors 23 and the one-dimensional collimator 24 are combined forms the two dimensional collimator.

In addition, the γ-ray detector 3 is formed by a γ-ray detector module 40, the γ-ray detector 3 is circularly disposed opposite to a regulated tomogram surface and is stacked for several layers along a body axis direction of the test subject 2.

Figure 11:
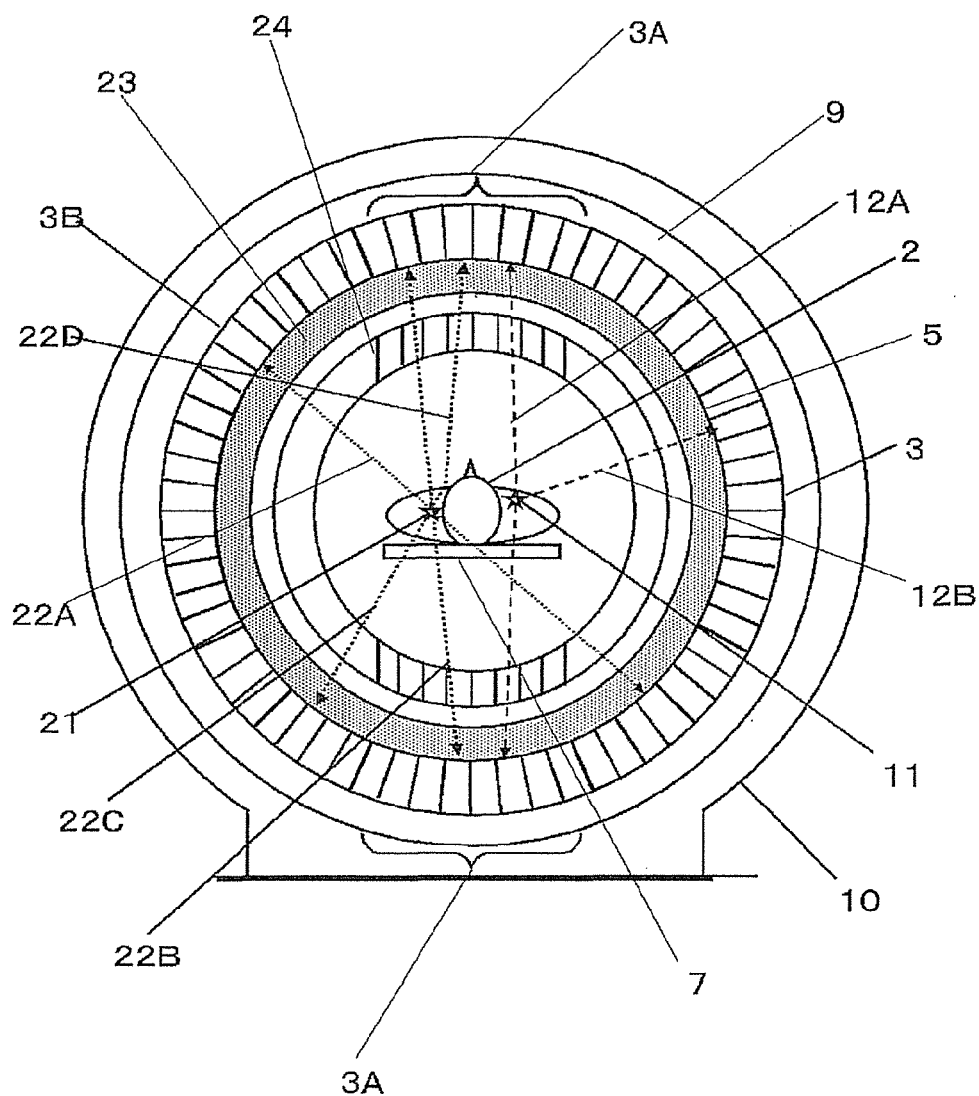
FIG. 11 is a front sectional view of the nuclear medical diagnostic device according to the second embodiment of the present invention.

In another aspect, FIG. 11 is a front sectional view of the nuclear medical diagnostic device 1 of the present invention. The one-dimensional collimator 24 of FIG. 11 may be rotated along the front of the γ-ray detector 3, and the γ-ray detector 3 is circularly disposed opposite to the regulated tomogram surface. Further, the one-dimensional collimator 24 only resides on a part of the entire periphery, and is arranged, for example, in opposite positions. The ceptors 23 and the one-dimensional collimator 24 form the two dimensional collimator, so as to detect the single photon γ-ray 12. In other words, when the one-dimensional collimator 24 is rotated, a γ-ray detector 3A located in an instant area where the γ-ray detector 3 is overlapped, the ceptors 23 and the one-dimensional collimator 24 function together, so as to detect the single photon γ-ray 12, in which the γ-ray detector 3 is circularly disposed opposite to the regulated tomogram surface. All the γ-ray detectors 3 detect annihilation γ-rays 22 generated from the positrons.

In one aspect of the invention, the γ-ray detector module 40 forming the γ-ray detector 3 is composed of scintillators, a light guide, and photomultipliers, in which the scintillators will emit light after the γ-rays emitted from the radioactive agent in the test subject are incident thereon, the light guide is used to specify the position, and the photomultipliers convert the light emitted by the scintillators to a pulse electric signal. The details of this embodiment are the same as those of the first embodiment.

Then, in order to detect the accumulation portions of the agents, the annihilation γ-ray and the single photon γ-ray must be totally discriminated for detection, and the details are the same as those of the first embodiment.

INDUSTRIAL AVAILABILITY

The present invention is applicable to the following nuclear medical diagnostic device (ECT device). The nuclear medical diagnostic device is used to simultaneously measure a γ-ray or a pair of γ-rays emitted by the single photon radioactive isotopes (RIs) or the positron RIs accumulated in the test subject, so as to obtain a tomogram of the target portion.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A nuclear medical diagnostic device, comprising:
    a plurality of γ-ray detectors, circularly disposed, and converting incident γ-rays to electric signals;
    a collimator unit comprising a one dimensional collimator arranged along a front of the plurality of the γ-ray detectors in a rotatable manner and one dimensional collimator having a shielding material arranged in a direction and residing on a part of a peripheral of the plurality of the γ-ray detectors and shielding a part of single photons, and a plurality of ceptors fixed on a whole periphery in the front of the plurality of γ-ray detectors, wherein the ceptors and the shielding material of the one dimensional collimator are combined to form a two dimensional collimator, wherein the two dimension collimator has a shielding material formed into a lattice shape;
    a collimator position detecting mechanism, detecting a position of the collimator;
    a simultaneous measuring mechanism, outputting the electric signals about simultaneously output from the plurality of γ-ray detectors as simultaneous measuring signals;
    an energy discriminating mechanism, discriminating first signals and second signals among the electric signals output from the plurality of γ-ray detectors, wherein the first signals are generated by the single photons emitted from a first agent accumulated in a test subject, and the second signals are generated by positrons emitted from a second agent accumulated in the test subject;
    a first position specifying mechanism, specifying a position of the first agent accumulated in the test subject according to the first signals and the position of the collimator; and
    a second position specifying mechanism, specifying a position of the second agent accumulated in the test subject according to the simultaneous measuring signals and the second signals,
    wherein the positions of the first agent and the second agent are simultaneously specified.

2. The nuclear medical diagnostic device according to claim 1, wherein
    the energy discriminating mechanism further comprises a scattered ray removing mechanism, and the scattered ray removing mechanism removes the signals that are about simultaneously measured by two γ-ray detectors among the plurality of γ-ray detectors from the first signals, so as to reduce an influence due to a scattered ray of an annihilation γ-ray generated by the positrons emitted from the second agent accumulated in the test subject.

* * * * *